United States Patent [19]

Davis

[11] Patent Number: 5,372,589
[45] Date of Patent: Dec. 13, 1994

[54] FENESTRATED TRANSPARENT CATHETER SECURING DEVICE AND METHOD

[76] Inventor: W. Gordon Davis, 8410 Santa Clara, Frisco, Tex. 75034

[21] Appl. No.: 157,669

[22] Filed: Nov. 24, 1993

[51] Int. Cl.$^5$ .............................................. A61M 25/02
[52] U.S. Cl. ........................................ 604/180; 604/174
[58] Field of Search ............... 604/174, 177, 180, 179; 128/DIG. 26

[56] References Cited

U.S. PATENT DOCUMENTS

| | | | |
|---|---|---|---|
| 3,645,835 | 2/1972 | Hodgson | 161/146 |
| 3,782,377 | 1/1974 | Rychlik | 604/180 |
| 3,918,446 | 11/1975 | Buttaravoli | 127/133 |
| 4,059,105 | 11/1977 | Cutruzzula et al. | 128/133 |
| 4,275,721 | 6/1981 | Olson | 604/180 |
| 4,397,641 | 8/1983 | Jacobs | 604/180 |
| 4,614,183 | 9/1986 | McCracken et al. | 604/180 |
| 4,633,863 | 1/1987 | Filips et al. | 128/165 |
| 4,669,458 | 6/1987 | Abraham et al. | 128/133 |
| 4,678,462 | 7/1987 | Vaillancourt | 604/180 |
| 4,699,616 | 10/1987 | Nowak et al. | 604/180 |
| 4,838,868 | 6/1989 | Forgar et al. | 604/180 |
| 4,869,719 | 9/1989 | Hogan | 604/174 |
| 4,874,380 | 10/1989 | Hesketh | 604/180 |
| 4,883,053 | 11/1989 | Simon | 128/303 |
| 4,898,587 | 2/1990 | Mera | 604/174 |
| 4,919,654 | 4/1990 | Kalt | 604/180 |
| 4,966,590 | 10/1990 | Kalt | 604/180 |
| 5,074,847 | 12/1991 | Greenwell et al. | 604/180 |
| 5,112,313 | 5/1992 | Sallee | 604/180 |
| 5,282,791 | 2/1994 | Lipton et al. | 604/180 |

OTHER PUBLICATIONS

"Transparent Polyurethane Film as an Intravenous Catheter Dressing" Karen K. Hoffman et al., Journal AMA, Apr. 15, 1992, vol. 267, No. 15, p. 2072.
"Crystal Medical Products, Inc.'s Arterial Bandage", (Product Profile Advertisement), Anesthesiology Product News, 1993, vol. 2, No. 2, p. 13.

*Primary Examiner*—Paul J. Hirsch
*Attorney, Agent, or Firm*—Charles C. Garner

[57] ABSTRACT

A transparent, self-adhesive film dressing with a special aerating fenestra, is provided for efficiently securing an percutaneous catheter to the skin of the patient, for continual and complete visual inspection of the insertion penetration site and catheter, without encouraging growth of bacteria. The film is configured with an open aperture located directly over and surrounding the insertion penetration site, to provide continual aeration and allow the incision site to remain uncovered and accessible to ambient air, and thus remaining dry, preventing accumulation and maintenance of a warm moist environment, discouraging growth of bacteria, and decreasing relative risk of penetration site infection. The surrounding film is transparent for visual inspection, and is adhesive and large enough to serve as an efficient anchor to prevent accidental dislodgement of the catheter, but is no longer an infection hazard.

19 Claims, 1 Drawing Sheet

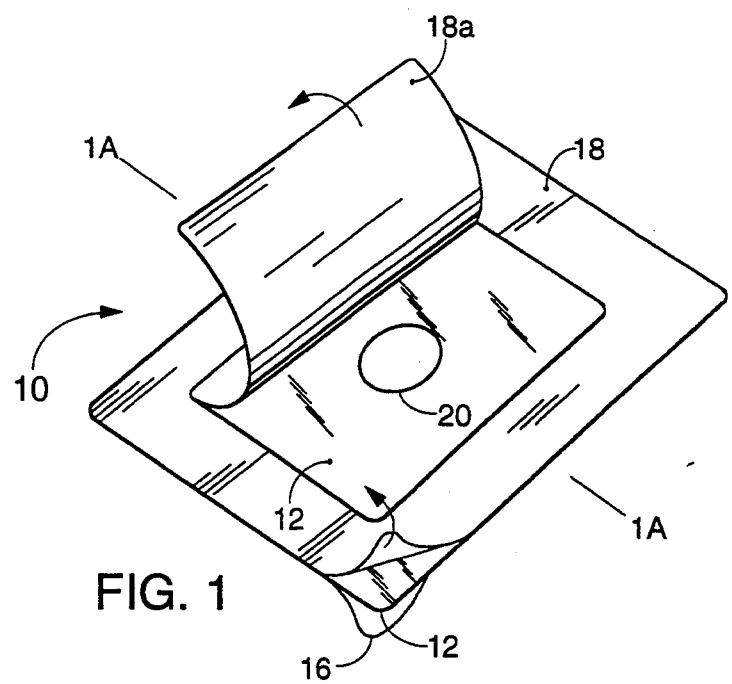
FIG. 1
FIG. 1A
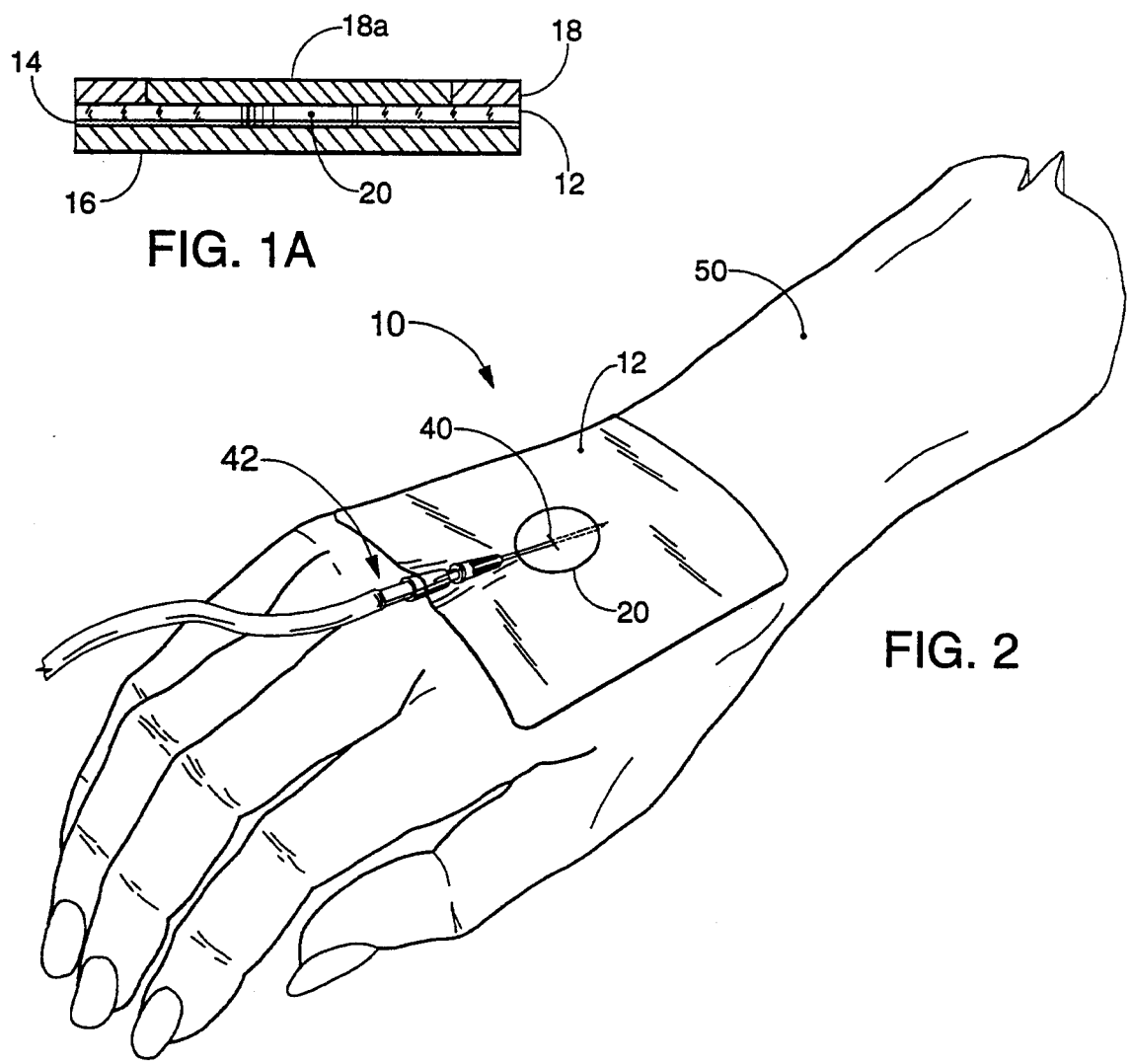
FIG. 2

FENESTRATED TRANSPARENT CATHETER SECURING DEVICE AND METHOD

TECHNICAL FIELD

This invention pertains to the field of medical equipment for efficiently securing a catheter, needle or cannula to a patient while reducing the relative risk of infection.

BACKGROUND OF INVENTION

General Background

Medical practice requires devices for attaching and securing a needle, catheter or cannula to a patient for intravenous injections, blood transfusions, anesthesiology, drainage or feeding, and other percutaneous intubations. In general, experience has shown that such devices should preferably provide the following characteristics:

clean and sterile;
comfortable for the patient;
secure in attaching and holding the catheter safely to prevent accidental removal or disengagement;
resilience to absorb some degree of movement without damage or discomfort to the patient;
provide visibility for continuing inspection;
efficient to apply, use, remove, and replace;
inexpensive; and
without increasing the relative risk of infection.

Many types of catheter attaching devices are available in this field; yet few, if any, efficiently provide these desirable characteristics. Many are deficient or inefficient in one or more capabilities, requiring medical practitioners to compromise for particular circumstances.

Basically, a catheter can be, and often is, secured with conventional medical adhesive tape and auxiliary materials. A gauze pad is positioned at the point of penetration, and strips of adhesive tape are torn and applied to the pad, catheter and tubing in a manner calculated to minimize risk of accidental injury or removal of the needle from the patient by inadvertent movement.

In many instances, if protective schemes have been used, they have consisted of temporary use of available materials such as towels and portions of styrofoam cups held in place with adhesive tape. Such schemes are clumsy and obstruct visual inspection of the needle or area of injection as well as requiring untaping of the temporary protector to make certain of the well being of the patient and the security of the catheter. Other devices place pressure or strain on the intravenous needle rather than providing protection.

The effectiveness of these contrived methods, including number of strips of tape, manner of applying them, and degree of protection, depends on the skill and ingenuity of the medical practitioner in applying the tape and materials. Thus adhesive tape attachment is time consuming, inefficient and expensive, can be clumsy to use and replace, and most often obstructs the view and precludes ready visual inspection. Viewing of the penetration incision is dependant upon the pattern of which the attendant applies the devices and strips of tape, as well as the size and arrangement of the gauze pad. By obscuring visibility of the penetration site, infiltration and infection may be undetected. Many types of schemes and attaching apparatus have been devised and are available in attempts to solve this problem, with varying complexities.

Prior Devices for Attaching Catheters

Buttaravoli U.S. Pat. No. 3,918,446 uses a sandwich design of pads to hold the catheter, which must be moved underneath and the inserted needle arranged between the layers, requiring delicate movement of the catheter. The pads obscure visibility of the needle and significant area surrounding the catheter.

Cutruzzula U.S. Pat. No. 4,059,105 uses a unitary T-shaped, laminated, folded harness, having a narrow, lower body portion 12 with an elongated opening 16 to expose the insertion site at which the cannula 34 enters the patient, and a wide, upper head portion 14 which is then folded and superimposed upon the narrow portion 12, to secure the catheter and cover the opening 16. The structure and adhesive are opaque and obstruct visibility of the penetration site and apparatus, although the opening 16 of the site and cannula 34 may be viewed when the upper portion 14 is unfolded for inspection.

Jacobs U.S. Pat. No. 4,397,641 uses a rigid annular support plate 30 and pad 46, securable to the patient by an adhesive patch 50, and having an inclined catheter support bracket 40, and arcuate passageway for mechanically isolating the catheter tubing. It has concentric apertures 44 and 48 for an open area of the patient's skin through which the cannula is inserted, although Jacobs appears not to recognize the need for aerating the site to ambient air to inhibit risk of infection, and teaches away from such advantage by noting in column 4 line 63 that the entire area over the puncture site may be protected by gauze and tape as needed in order to maintain the puncture site free of contamination, and tape may be periodically removed for inspection.

Filips et al U.S. Pat. No. 4,633,863 discloses an arterial anchor bandage which emphasizes need for visible inspection, but includes opaque structures which obstruct from view the skin surrounding a puncture site. Filips recites need for circulation of air at penetration site, but is a closed bandage which provides only pores for restricted air circulation. Filips discloses a transparent bulbous shield 12 which permits some amount of visible inspection, which protrudes above a tri-lobed adhesive outercovering layer 18, and which has an opening 14 sized to receive the tube from an arterial catheter and to permit rotation of the catheter without removal of the bandage to check positionality of catheter. Various features of the structure permit its application very close to articulated joints at radial, brachial and femoral sites of a patients anatomy. In comparison, Davis' instant invention of this application provides structural simplicity which permits the Davis device to be applied anywhere. Filips recites that air circulation aids in healing and keeps the skin healthy, but Filips makes only the outer cover of porous material and may alternatively be provided with a plurality of pores which permits only restricted ability to circulate air (efficacy unknown) and reduce moisture buildup. Filips teaches use of an absorbent layer 28 between the shield 12 and the skin of the patient to provide a wicking function to remove fluids from the insertion area; whereas Davis' device provides entirely open access to air circulation and aeration by virtue of its totally open center.

Abraham U.S. Pat. No. 4,669,458 discloses a holder 10 with a flat base 12 and adhesive bottom with a aperture 16 in the middle, having a clear plastic, replaceable window 14 with adhesive bottom 22 placed over the aperture, so that the insertion site lies in the middle of the aperture, and the clear window covers and protects the needle, allowing the insertion site to be observed. A see-through gauze pad 28 with antibiotic salve may be removably placed underneath the clear window. It is also possible to use a plastic material such as Saranwrap for the window 14. Abraham includes opaque structure which obstructs vision of the site; provides no aeration; and teaches away from aeration by providing clear plastic covers 14 over the needle insertion site.

Nowak U.S. Pat. No. 4,699,616 provides an adhesive barrier pad 11, with an opening 14 aligned with the fenestration in the body wall, the pad 11 having a molded plastic catheter support structure 12 and a planar base 21, two support arms 24a and b, and a pair of elongated clamping bars 25 and 26 for clamping the catheter. Slits 15 and 22 are provided for spreading the edges of the pad 11, base 21, and entry slit 15, and urging the catheter laterally into the opening 14, exposing the area of the incision for inspection; but the structure, base, pad, adhesive and apparatus assembly are opaque, obstructing view of the site; require maneuvering for assembly and obstruct and impair visibility. Nowak does not teach aeration of the penetration site; uses a pressure sensitive adhesive which in column 3 line 30 preferably also performs a sealing function in protecting the skin against fluid contact; and in column 6 line 9 provides that a nurse or doctor might cut the pad to form a central opening of greater size to suit the particular catheter exit site.

Hogan U.S. Pat. No. 4,869,719 provides a plastic retaining plate 52 anchored to the patient's skin 26 with adhesive, having a cover 62 for a chamber for packing gauze 66 where the catheter enters the patient, with bushings, sleeves, and spacers to adjust length of the inserted catheter. A cut 60 in the retaining plate 62 permits the threading of the catheter tube 20 through the aperture 58 and the positioning of the bushing 28. Relatively small openings 64 in the cover 62 permit only limited and obstructed visual inspection of the cotton gauze 66 so that it can be replaced when necessary, and also provides for limited amount of aeration of the incision, but does not teach combined visibility and aeration to inhibit bacteria.

Hasketh U.S. Pat. No. 4,874,380 discloses a flange 10 having a central hole 12, mounted on a pad 14, with an upstanding post 16, with an elongated tab 22, ratchet teeth 24, and detente 28, for griping the catheter, and a slit extending from the hole 22 to its periphery for introducing the catheter and tubing without having to thread the whole length through the device. In Hasketh, the central hole 12 is only somewhat larger than the diameter of the catheter.

Simon U.S. Pat. No. 4,883,053 provides a retractable, foldable, self-supporting, angulator device, for precise angular aiming, holding and percutaneous insertion of surgical objects such as a needle into the tissues of a subject. The base plate 12 with center aperture 20 will be positioned at the insertion site overlying the tissue to be penetrated, adjustably holding the needle at precise angle for insertion through center aperture 20.

Kalt U.S. Pat. Nos. 4,919,654 and 4,966,590 disclose a clamp for holding a catheter, a flap, securing surfaces, and a resilient pad for adhering to the patient. The resilient pad is deformable such that slight rotation or translational movement will deform the pad rather than breaking the adhesive bond between. The base has a window for positioning the clamp on the patient with the intravenous puncture positioned for view through the window 17, with a sterile, breathable, clear, waterproof membrane 15, covering the window opening 17 and having a slot for allowing a needle to puncture a patient's skin at a point located under the membrane. The membrane 15 seals and protects the skin puncture 90 by the needle 91, which extends through the membrane 15 at puncture hole 18. Kalt discloses that a resilient adhesive pad in contact with an IV needle structure provides secure means for holding the catheter and tube against rotational or translational movement, tending to deform, twist, and move with the catheter and tube when urged to rotate slightly. Kalt does not teach visibility combined with open aeration to inhibit growth of bacteria.

Sallee U.S. Pat. No. 5,112,313 shows a molded, plastic cover, that is transparent so that one can see through the thin walled body 14, to view the needle catheter secured inside and attached to the patient with adhesive tape. There can be openings 28 in the roof 26 of the housing 12, to provide a limited amount of air circulation to the hollow area within the housing 12. The cover or roof may be hinged so that access to the intravenous needle can be had without removing the adhesive tape. The roof can have transparent magnification to enable viewing of the intravenous needle insertion site.

Several manufacturers market self-adhesive sterile, transparent plastic film as a covering for wounds and incisions. One such material is covered by Hodgson U.S. Pat. No. 3,645,835 which discloses a moisture-vapor-permeable, pressure-sensitive adhesive material as a surgical drape, suture strip, adhesive dressing, bandage, plaster, tape, etc., comprising a backing material and pressure sensitive adhesive on one surface, being both moisture-vapor-permeable and unaffected by water and nonpermeable to liquid water. Such materials are useful where it is desirable to have an adhesive material which is permeable to water vapor, but which is not permeable to liquid water, micro-organisms, and particles of dirt, in order to provide the desired covering without causing maceration, steeping and wasting-away, due to occlusion of water from transepidermal water loss from the body.

The 3-M Company, Medical-Surgical Division, has marketed a self-adhesive sterile, transparent plastic film intended as a medical dressing. The 3-M product is marketed as Tegaderm TM material under license from Hodgson U.S. Pat. No. 3,645,835. Another product of this type is marketed as BIOCLUSIVE ® Transparent Dressing, a Johnson & Johnson trademark, by MEDI-FLEX⊗, Overland Park, Kans. 66210. Similar commercial materials are believed to be available from other sources. These materials have the advantages of being non-complex, transparent for visual inspections, and securely adhering and covering medical applications, and some are permeable to water vapor, thus providing visual inspection, keeping the application clean, and avoiding maceration.

Experimentation with Transparent, Self-Adhesive Film as an Attachment Device for Securing Catheters There has been experimentation in use of self-adhesive sterile, transparent plastic materials as means to secure intravenous catheters to the body of the patient. A solid rectangular or circular sheet of the transparent self-adhesive film has been used, large enough to bind the catheter to the patient's skin, covering a substantial portion of the catheter and surrounding skin of the patient. The sheet of film is applied directly over the catheter site and skin, so that the adhesive film securely grips the structure of the catheter, including in some cases also part of the attached tubing, and as much of the patient's body as is desired by the medical practitioner.

Recognizing the Problem with Transparent Film

Initially, transparent film material appeared to provide a desirable device for securing medical catheters. The tenacity of the adhesive, and the resilience, and somewhat flexibility, of the material, appeared to provide a secure and shock absorbing attachment. Transparent film material is transparent, sterile, less complex, easier to use and less expensive than prior devises and methods.

However, for percutaneous injections, these transparent film materials suffer a serious disadvantage. All of them double or triple the intravenous site infection rate due to the maintenance of a warm moist environment under the plastic film, which encourages growth of bacteria at the site. Consequently, in spite of ready commercial availability of this material, and in spite of its ease of use and obvious mechanical advantages as an efficient and transparent attaching device for catheters and cannulas, such uses, as previously configured, have been reported by the Journal, American Medical Association, to involve significant increase in relative risk of infection.

In medical publication, "Transparent Polyurethane Film as an Intravenous Catheter Dressing", by Karen K. Hoffman et al., Journal American Medical Association, Apr. 15, 1992, Vol. 267, No. 15, page 2072, it was reported that "use of transparent dressings on central venous catheters was significantly associated with an elevated relative risk (RR) of catheter-tip infection . . . Catheter-related sepsis . . . and bacteremia . . . were both associated with an elevated RR. Use of transparent dressings on peripheral catheters was associated with an elevated RR on catheter-tip infection . . . but not phlebitis . . . , infiltration . . . , or skin colonization . . . The results demonstrated a significantly increased risk of catheter-tip infection with the use of transparent compared with gauze dressings when used with either central or peripheral catheters. An increased risk of bacteremia and catheter sepsis associated with the use of transparent compared with gauze dressings for use on central venous catheters was suggested."

The report stated "The mechanism by which transparent dressings increase catheter-associated infection is likely the promotion of bacterial growth (Aly R., Shirley C., Cinico B., Maibach Hi. Effect of prolonged occlusion on the microbial flora, pH, carbon dioxide and transepidermal water loss on human skin. J. Invest Dermatol. 1978; 71:378–381.), which may be related to the inadequate moisture vapor permeability. (Craven Del., Lichtenberg DA, Kunches M, et al. A randomized study comparing a transparent polyurethane dressing to a dry gauze dressing for peripheral intravenous catheter sites. Infect Control. 1985; 6:361–366.)"

The report further concluded "Based on our data, we suggest that the increased infection risks associated with transparent dressings be considered an institutional decision . . . New, more permeable dressings may result in reducing the infection risks associated with this type of dressing."

Solution to the Problem; and Concept of the Invention

This Applicant has found and herein discloses that permeability, porosity, and even perforation of the transparent, adhesive dressing materials is not enough— —the solution to this problem is to keep the immediate penetration site open to ambient air which will aerate the site and tend to keep it dry, thus inhibiting growth of bacteria. The solution involves a conceptual change in the design and configuration of the transparent, self-adhesive film dressings to be used as a securing device. The film must remain transparent for inspection, and must substantially cover, efficiently adhere, and secure the catheter to the skin of the patient. But, to inhibit growth of bacteria and reduce the relative risk of infection, continual and substantially open, fenestra aeration must be provided to the penetration site. The open aperture must be large enough to allow the site to remain dry. In this manner, it is hereby disclosed that the many advantages of transparent self-adhesive film may be safely and prudently used while avoiding the problems of increased relative risk of infection. These are major advantages which surpass prior devices. The resilient material tends to act with the patient's skin to absorb deflections and move with the catheter and tube when urged to rotate or translate slightly. Significant movement of the catheter tube is possible without degrading the integrity of the bond. The material conforms and adheres tenaciously to the shape of the patient's body in various, nonuniform positions, as in attachment to the back of a hand. And it is painless for the patient, is efficient and easy to apply, use, remove and replace, is sterile, clean and disposable, is inexpensive, and by all means it is entirely transparent and provides excellent visibility at all times for continual inspection of the penetration site, catheter, tubing, surrounding area of the site, and general well being of the patient. And it provides means to inhibit warm moist buildup, to avoid encouraging bacterial growth.

Packaging for this fenestrated transparent catheter securing device may be provided in various equivalent designs, the purpose being to physically protect the film and its adhesive side, keeping it sterile and clean, during transportation and handling, and during immediate application of the film to the penetration site. A preferred packaging and method is disclosed herein in which the packaging also provides an efficient method of handling, using the packaging as a handling frame and means for aiming and efficiently targeting the penetration site during the application of the film dressing.

These many advantages may be realized for anchoring catheters without the hazard of infection, by use of the device and method disclosed in this invention.

BRIEF SUMMARY OF THE INVENTION

This catheter securing device is a transparent, self-adhesive film dressing with a special, aerating fenestra, which substantially covers, adheres, attaches and secures an intravenous catheter to the skin of the patient, for visual inspection, without encouraging growth of bacteria. The film is configured with an open aperture located directly over and surrounding the insertion penetration site of the needle, to provide continual aeration, allowing the incision site to remain uncovered and accessible to ambient air, thus remaining dry and preventing accumulation and maintenance of a warm moist environment, discouraging growth of bacteria, and not increasing relative risk of intravenous site infection.

DESCRIPTION OF THE DRAWINGS

Referring now to the Drawings, please notice that like reference numbers in each of the FIGS. 1-2 are used to designate like, corresponding or equivalent parts throughout all views of the accompanying Drawings, wherein:

FIG. 1 provides a perspective view of the medically sterile, fenestrated transparent catheter securing device 10, enclosed in preferred but optional packaging. FIG. 1A is a cross section view through section line 1A—1A, of optional but preferred packaging, showing layered disposition of the film 12, with open fenestra 20, as protected by peel-away protective cover 18, with peel-away protective door 18A, adhesive coating 14 on the bottom surface of film 12, and peel-away protective backing sheet 16.

FIG. 2 is a perspective view of the hand of a medical patient 50, showing the intravenous catheter 42, inserted into the puncture site 40, with the catheter securing device 10 providing transparent attachment of the catheter 42 to the skin of the patient 50. Aeration is provided by the fenestra 20.

DESCRIPTION OF INVENTION DEVICE, AND METHOD

The fenestrated transparent catheter securing device 10 is shown in FIG. 1, together with optional packaging to keep it clean and sterile, and to protect the adhesive lower surface of the film before use. The device 10 consists of a sheet of transparent film 12, which may be rectangular in shape, and equivalently may be circular, oval, or irregular in shape to accommodate for attachment to the area and shape of the body of the patient. The lower surface of the film sheet 12 is coated with a transparent adhesive 14. The open aerating fenestra 20 is shown in the central part of transparent film 12. Preferred packaging, not essential to this disclosure but preferred, will consist of protective materials such as a peel-away protective backing sheet 16, and a peel-away protective cover sheet 18 with peel-away door 18a.

For illustration, the fenestrated transparent catheter securing device 10 is shown here in FIG. 2 as applied to the hand 50 of a medical patient. Catheters for hands, arms, feet, legs, and like appendages of the body are known as peripheral catheters, and this invention is equivalently applicable to peripheral catheters and to central catheters as well into the torso and central parts of the patient's body. In FIG. 2, the intravenous catheter 42 has been inserted into the penetration insertion site 40 in the body of the patient 50. It is the disclosure of this invention that, while the entire securing device must be transparent for visual inspection of the overall catheter and area, the immediate area of the needle insertion site 40 must be kept continually aerated with ambient air to keep the site dry. To accomplish this, the film 12 is provided with an open aerating fenestra 20, comprising an open aperture 20 located directly over and surrounding the immediate insertion penetration site 40 of the needle. The purpose of the open fenestra is to provide continual aeration and allow the incision site to remain dry, uncovered and accessible to ambient air, thus preventing accumulation and maintenance of a warm moist environment, discouraging growth of bacteria, and decreasing risk of intravenous site infection.

For application of the device 12, using the optional but preferred packaging of FIG. 1 and 1A, the following procedure is used. First remove the peel-away protective door 18a; then remove the peel-away protective backing sheet 16, exposing the adhesive coating 14 and leaving a stiff edged, transparent, clear centered, sticky bottomed, rectangle assembly with open fenestra 20 in the center. Use the clear centered rectangle with open fenestra 20 to look through and target the penetration site, as the film 12 is applied. When the film 12 is properly aligned so that the open fenestra 20 is directly over and around the insertion site, apply the film to the patient's skin. Use the stiff edged 18 to apply pressure so the film will adhere to the site, catheter and skin. Finally, remove the stiff edged peel-away protective cover 18, and application is complete.

The size of the aerating fenestra will ordinarily be about one inch in diameter, but will be sized proportional to the size and shape of the catheter and needle insertion site, to achieve efficient aeration, and must be large enough to keep the site dry. The size of the transparent film will be selected proportional to the size of the catheter, and equivalently at the option of the medical practitioner may cover part of the tubing for additional security; but the adhesive film must be large enough to substantially cover the catheter 42 and surrounding skin 50 of the patient's body for secure and resilient attachment.

The surrounding film 12 is transparent for visual inspection, and is adhesive on the bottom surface 14 and large enough to serve as an efficient anchor to prevent accidental dislodgement of the catheter, but is no longer an infection hazard.

It will be readily seen that the fenestrated transparent catheter securing device of this disclosed invention, has the characteristics of the ideal catheter securing device, is a significant advancement over the prior art, retains all of the advantages of simplicity, transparency and continual visual inspection capabilities of transparent film dressings, but overcomes disadvantages and does not increase relative risks of infection inherent in prior film dressings.

For ease of description, the drawings and explanations have been directed to a peripheral catheter, located in an appendage or extremity of the body such as a hand; but the advantages of this improved device have been found to be fully and equally applicable to central catheters, as well, located on the torso and main parts of the body. Likewise, these advantages are not limited to intravenous catheters, but are useful in a variety of medical needles, cannulas, tubes, and percutaneous catheters for various medical purposes in general.

Although the preferred embodiment has been described herein and in the drawings with specificity, it is intended and will be understood that the invention is not limited to this embodiment, but is capable of a number of equivalent designs, configurations and arrangements within the scope and spirit of the invention.

I claim:

1. A transparent fenestrated device for securing a catheter to a patient without increasing relative risk of infection, consisting of:

a single transparent film for covering a portion of the catheter and a portion of the patient's body;

said film comprising transparent adhesive for adhering said film to said catheter and body wherein said film comprises sole means for securing said catheter to said body;

said film shaped to form an open aperture of direct, unobstructed aeration over the skin penetration site of said catheter and said patient's surrounding skin;

and said open aperture of direct, unobstructed aeration being large enough to allow said site and skin to remain dry, comprising means for significantly inhibiting growth of bacteria.

2. A device according to claim 1 wherein said aperture is at least 15 millimeters in diameter.

3. A device according to claim 1 wherein said film and said adhesive comprise self-adhesive sterile, substantially transparent plastic film, permeable to moisture vapor but impermeable to liquid water, of a type intended as a covering for wounds and medical dressings.

4. A device according to claim 1 wherein said film and said adhesive further comprise means for securing part of the tubing of said catheter to said body.

5. A device according to claim 1 wherein said film further comprises packaging for handling said film, and wherein said packaging comprises means for visually targeting and positioning said film and aperture over said penetration site while applying said film to said catheter and body.

6. A device according to claim 5 wherein said packaging comprises:

a peel-away protective backing sheet on the adhesive side of said film; and a peel-away protective top sheet on the non-adhesive side of said film;

said top sheet comprising a stiff-edged peel-away frame and a separately removable, peel-away door; and comprising means for said door to be peeled away from said frame and non-adhesive side of said film, and for exposing to visibility the top central area of said film including said aperture; and comprising means for said backing sheet to be peeled away from said adhesive side of said film, for exposing said adhesive coating on the bottom of said film; and for leaving a stiff edged, non-sticky packaging frame on the non-adhesive side of said film, and a transparent, clear centered, sticky bottomed, film with said open aperture in said central area for targeting visibility.

7. A process for securing a catheter to a patient with transparent film without increasing relative risk of infection, comprising the steps of:

selecting transparent, self-adhesive film for covering a portion of the catheter and a portion of the patient's body;

shaping said film to form an open aperture over the skin penetration site of said catheter which provides direct, unobstructed aeration to said site when said film is applied to said catheter and body, for allowing said site and said patient's surrounding skin to remain dry wherein said film comprises means for significantly inhibiting growth of bacteria;

aligning and positioning said aperture over and around said penetration site when said film is covering said portion of said catheter and body; and applying and pressing said self-adhesive film into position onto said catheter and body, wherein said film adheres to said catheter and body and comprises sole means for securing said catheter to said body.

8. A process according to claim 7 further comprising the step of shaping said film to form said open aperture at least 15 millimeters in diameter.

9. A process according to claim 7 further comprising the step of selecting said film to comprise substantial permeability to moisture vapor and impermeability to liquid water.

10. A process according to claim 7 further comprising the step of selecting said film to comprise self-adhesive sterile, substantially transparent plastic film, that is permeable to moisture vapor but impermeable to liquid water, of a type intended as a covering for wounds and medical dressings.

11. A process according to claim 7 further comprising the step of adhering a portion of said self-adhesive film onto a portion of the tubing leading to said catheter comprising means for further securing said catheter.

12. A process according to claim 7 further comprising the step of selecting said film to comprise packaging for said film and the step of using said packaging as means for visual targeting and aligning said aperture over said penetration site during application of said film to said catheter and body.

13. A process according to claim 12 wherein said step of using said packaging as visual targeting means comprises the steps of removing the peel-away protective top door from said transparent film; removing the peel-away protective backing sheet, exposing the adhesive coating, leaving a stiff edged, transparent, central area of said film, with a sticky bottom and non-sticky top, with said open aperture in said central area; looking through said transparent central area and open aperture to target said aperture over and around said penetration site as said film is applied; aligning said film so that said open aperture is directly over and around said site; applying pressure to said stiff-edged frame so that said transparent film adheres to said catheter and body; and removing said stiff-edged peel-away protective top cover frame.

14. A device for securing a skin penetrating catheter to a patient without increasing relative risk of infection, consisting of:

a single transparent film for covering part of the catheter and part of the patient's body;

a transparent adhesive coating on the body contacting surface of said film for adhering said film to said body and said catheter wherein said film and said adhesive comprise sole means for securing said catheter to said body;

an unobstructed opening in said film over and around the skin penetration site of said catheter, directly aerating said site and the surrounding skin for allowing them to remain dry, comprising means for inhibiting growth of bacteria.

15. A device according to claim 14 wherein said unobstructed opening is not less than 15 millimeters in diameter.

16. A device according to claim 14 wherein said film and said adhesive comprise self-adhesive sterile, substantially transparent plastic film, that is permeable to moisture vapor but impermeable to liquid water, of a type intended as a covering for wounds and medical dressings.

17. A device according to claim 14 wherein said film and said adhesive further comprise means for securing part of the tubing of said catheter to said body.

18. A device according to claim 14 wherein said film and said adhesive further comprise packaging for handling said film, and wherein said packaging comprises means for visually targeting and positioning said film and aperture over said penetration site during application of said film to said catheter and body.

19. A device according to claim 14 wherein said packaging comprises:

a protective backing sheet on the adhesive side of said film; and a protective top sheet on the non-adhesive side of said film;

said top sheet comprising a stiff-edged frame and a separately removable, peel-away door; and means for said door to be peeled away from said frame and non-adhesive side of said film, for exposing to visibility the top central area of said film including said aperture; and means for said backing sheet to be peeled away from said adhesive side of said film, for exposing said adhesive coating on the bottom of said film; leaving a stiff edged, non-sticky packaging frame on the non-adhesive side of said film, and a transparent, clear centered, sticky bottomed, film with said open aperture in said central area for targeting visibility.

* * * * *